United States Patent
Womack et al.

(10) Patent No.: US 10,575,543 B2
(45) Date of Patent: *Mar. 3, 2020

(54) ACETALDEHYDE PRECURSORS

(71) Applicant: Firmenich SA, Geneva (CH)

(72) Inventors: Gary B. Womack, Plainsboro, NJ (US); Matthew Sillick, Belle Mead, NJ (US)

(73) Assignee: Firmenich SA, Satigny (CH)

( * ) Notice: Subject to any disclaimer, the term of this patent is extended or adjusted under 35 U.S.C. 154(b) by 240 days.

This patent is subject to a terminal disclaimer.

(21) Appl. No.: 15/538,116

(22) PCT Filed: Dec. 21, 2015

(86) PCT No.: PCT/EP2015/080718
§ 371 (c)(1),
(2) Date: Jun. 20, 2017

(87) PCT Pub. No.: WO2016/102425
PCT Pub. Date: Jun. 30, 2016

(65) Prior Publication Data
US 2017/0339993 A1    Nov. 30, 2017

Related U.S. Application Data

(60) Provisional application No. 62/096,835, filed on Dec. 24, 2014.

(51) Int. Cl.
| | | |
|---|---|---|
| *A23L 2/39* | (2006.01) | |
| *A23L 2/56* | (2006.01) | |
| *A23L 27/29* | (2016.01) | |
| *C07D 307/12* | (2006.01) | |
| *A23L 27/20* | (2016.01) | |

(52) U.S. Cl.
CPC ............ *A23L 27/2024* (2016.08); *A23L 2/39* (2013.01); *A23L 2/56* (2013.01); *A23L 27/29* (2016.08); *C07D 307/12* (2013.01)

(58) Field of Classification Search
CPC ........ A23L 27/2024; A23L 27/29; A23L 2/56; C07D 307/12
See application file for complete search history.

(56) References Cited

U.S. PATENT DOCUMENTS

| | | | |
|---|---|---|---|
| 3,764,567 A | 10/1973 | Wakayama et al. | |
| 3,931,250 A | 1/1976 | Thomas | |
| 5,079,023 A | 1/1992 | DeSimone | |
| 6,235,956 B1* | 5/2001 | Hugues | C07C 43/303 585/511 |
| 2005/0026998 A1 | 2/2005 | Womack et al. | |
| 2017/0369461 A1* | 12/2017 | Normand | A23L 27/2024 |
| 2018/0103667 A1* | 4/2018 | Womack | A23L 27/2024 |

FOREIGN PATENT DOCUMENTS

JP    1984130879 A    7/1984

OTHER PUBLICATIONS

Lukic et al "Characterization and Differentiation of Monovarietal Grape Marc Distillates on the Basis of Varietal Aroma Compound Composition", Journal of Agricultural and Food Chemistry, 2010, 58(12), pp. 7351-7360.*
International Search Report and Written Opinion, application PCT/EP2015/080718 dated Apr. 7, 2016.
Williams et al, "Hydroxylated Linalool Derivatives as Precursors of Volatile Monoterpenes of Muscat Grapes," J. Agric. Food Chem., vol. 28, No. 4, 1980, pp. 766-771.
Furia et al, "Fenaroli's Handbook of Flavor Ingredients," XP-002102351, 1975, pp. 543, 656.

* cited by examiner

*Primary Examiner* — Michele L Jacobson
*Assistant Examiner* — Changqing Li
(74) *Attorney, Agent, or Firm* — Armstrong Teasdale LLP

(57) ABSTRACT

Provided herein is 5-(2-(1-ethoxyethoxy)propan-2-yl)-2-methyl-2-vinyltetrahydrofuran and its use as a flavor and aroma modifier in foods and beverages.

5 Claims, No Drawings

ACETALDEHYDE PRECURSORS

This application is a 371 filing of International Patent Application PCT/EP2015/080718 filed 21 Dec. 2015, which claims the benefit of US patent application No. 62/096,835 filed Dec. 24, 2014.

FIELD

Provided herein is a precursor to acetaldehyde and its use for delivering acetaldehyde to food and beverages to typically provide increase flavor.

BACKGROUND

Acetaldehyde is an important yet difficult to encapsulate flavor ingredient. It is used in a large variety of flavors but is particularly appreciated in fruit flavors where it imparts important aspects of freshness and juiciness to the flavors. The volatility of acetaldehyde also provides lift to the aroma greatly contributing to the olfactive impact of the flavor. Thus the use of acetaldehyde is indispensable for creasing flavors where these effects are desired such as in beverages. However, with a boiling point of 20-21° C., it is a difficult material to use due to evaporation during handling which in turn can create unsafe situations due to overexposure to personnel and the risk of fire. Once incorporated into a liquid flavor loss of acetaldehyde due to evaporation is still a concern which also can make handling such flavors difficult. In addition to being highly volatile, acetaldehyde is a very reactive chemical. It can react with alcohols in flavor formulations to form acetals; it can engage in aldol condensation reactions; it is susceptible to oxidation; and it can trimerize to form paraldehyde. In addition to losing acetaldehyde by these chemical reactions, the products formed can change the character of the flavor and in the worst case contribute unwanted off-flavors.

SUMMARY

Provided herein is 5-(2-(1-ethoxyethoxy)propan-2-yl)-2-methyl-2-vinyltetrahydrofuran, represented by the formula

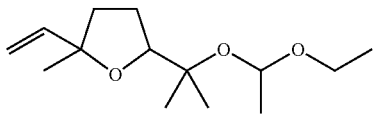 [SMILES: C=CC1(C)CCC(C(C)(C)OC(C)OCC)O1]

Also provided herein is a method of releasing acetaldehyde into an aqueous solution comprising delivering 5-(2-(1-ethoxyethoxy)propan-2-yl)-2-methyl-2-vinyltetrahydrofuran.

Still yet further provided herein is a flavor or aroma-modifying composition comprising:
i) 5-(2-(1-ethoxyethoxy)propan-2-yl)-2-methyl-2-vinyltetrahydrofuran,
ii) at least one ingredient selected from the group consisting of a flavor carrier and a flavor base; and
iii) optionally at least one flavor adjuvant.

DETAILED DESCRIPTION

By "flavor carrier" we mean here a material which is substantially neutral from a flavor point of view, insofar as it does not significantly alter the organoleptic properties of flavoring ingredients. The carrier may be a liquid or a solid.

Suitable liquid carriers include, for instance, an emulsifying system, i.e. a solvent and a surfactant system, or a solvent commonly used in flavors. A detailed description of the nature and type of solvents commonly used in flavors cannot be exhaustive. Suitable solvents include, for instance, propylene glycol, triacetin, triethyl citrate, benzylic alcohol, ethanol, vegetable oils or terpenes.

Suitable solid carriers include, for instance, absorbing gums or polymers, or even encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stahilisatoren, Dickungs—und Gehermittel in Lebensmittel, Band 2 der Schriflenreihe Lebensmittelchemie, Lebensmittelqualität, Behr's Verlag-GmbH & Co., Hamburg, 1996. Encapsulation is a well-known process to a person skilled in the art, and may be performed, for instance, using techniques such as spray-drying, agglomeration, extrusion, coacervation and the like.

In one embodiment, the compounds provided herein are provided in a "flavor Base" i.e., a composition comprising at least one additional flavoring ingredient. Said additional flavoring ingredient is not 5-(2-(1-ethoxyethoxy)propan-2-yl)-2-methyl-2-vinyltetrahydrofuran. Moreover, by "flavoring ingredient" it is meant here a compound, which is used to flavoring preparations or compositions to impart a hedonic effect. In other words such an ingredient, to be considered as being a flavoring one, must be recognized by a person skilled in the art as being able to impart or modify in a positive or pleasant way the flavor or aroma of a composition, and not just as having a flavor or aroma.

The nature and type of the flavoring co-ingredients present in the base do not warrant a more detailed description here, the skilled person being able to select them on the basis of his/her general knowledge and according to intended use or application and the desired organoleptic effect. In general terms, these flavoring co-ingredients belong to chemical classes as varied as alcohols, aldehydes, ketones, esters, ethers, acetates, nitrites, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of flavor. It is also understood that said co-ingredients may also be compounds known to release in a controlled manner various types of flavoring compounds.

By "flavor carrier" we mean here a material which is substantially neutral from a flavor point of view, insofar as it does not significantly alter the organoleptic properties of flavoring ingredients. The carrier may be a liquid or a solid.

Suitable liquid carriers include, for instance, an emulsifying system, i.e. a solvent and a surfactant system, or a solvent commonly used in flavors. A detailed description of the nature and type of solvents commonly used in flavor cannot be exhaustive. Suitable solvents include, for instance, propylene glycol, triacetin, triethyl citrate, benzylic alcohol, ethanol, vegetable oils or terpenes.

Suitable solid carriers include, for instance, absorbing gums or polymers, or even encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs—and Gehermittel in Lebensmittel, Band 2 der Schriftenreihe Lebensmittelchemie, Lebensmittelqualität, Behr's Verlag-GmbH & Co., Hamburg, 1996. Encapsulation is a well-known process to a person skilled in the art, and may be performed, for instance, using techniques such as spray-drying, agglomeration, extrusion, coacervation and the like.

A composition consisting of at least one compound of 5-(2-(1-ethoxyethoxy)propan-2-yl)-2-methyl-2-vinyltetrahydrofuran and at least one flavor carrier represents a particular embodiment of the invention as well as a flavoring composition, comprising at least one compound of 5-(2-(1-ethoxyethoxy)propan-2-yl)-2-methyl-2-vinyltetrahydrofuran, at least one flavor carrier, at least one flavor base, and optionally at least one flavor adjuvant.

Moreover, 5-(2-(1-ethoxyethoxy)propan-2-yl)-2-methyl-2-vinyltetrahydrofuran can be advantageously incorporated into flavored articles to positively impart, or modify, the flavor, freshness, the fruitiness, the juiciness or aroma of said articles. Thus, in yet another aspect, the present invention provides a flavored article comprising 5-(2-(1-ethoxyethoxy)propan-2-yl)-2-methyl-2-vinyltetrahydrofuran and a foodstuff base.

For the sake of clarity, it has to be mentioned that, by "foodstuff" we mean here an edible product, e.g. a food or a beverage. Therefore, a flavored article according to the invention comprises one or more compounds according to 5-(2-(1-ethoxyethoxy)propan-2-yl)-2-methyl-2-vinyltetrahydrofuran, as well as optional benefit agents, corresponding to flavor or aroma and flavor or aroma profile of the desired edible product. The compositions and methods provided herein have use in food or beverage products. When the food product is a particulate or powdery food, the dry particles may easily be added thereto by dry-mixing. Typical food products are selected from the group consisting of an instant soup or sauce, a breakfast cereal, a powdered milk, a baby food, a powdered drink, a powdered chocolate drink, a spread, a powdered cereal drink, a chewing gum, an effervescent tablet, a cereal bar, and a chocolate bar. The powdered foods or drinks may be intended to be consumed after reconstitution of the product with water, milk and/or a juice, or another aqueous liquid.

Suitable foodstuff bases, e.g. foods or beverages, include dairy and confectionary products where a fresh or fruity tonality is desired. In another embodiment provided herein is a dairy product including but not limited to non-frozen, partially frozen and frozen fluid dairy products such as, for example, milks, ice creams, sorbets and yogurts.

In one embodiment, the compositions and compounds provided herein provide "fresh", "juicy" and "fruity" flavor and/or aroma to a food article.

Beverage products include, without limitation, carbonated soft drinks, including cola, lemon-lime, root beer, heavy citrus ("dew type"), fruit flavored and cream sodas; powdered soft drinks, as well as liquid concentrates such as fountain syrups and cordials; coffee and coffee-based drinks, coffee substitutes and cereal-based beverages; teas, including dry mix products as well as ready-to-drink teas (herbal and tealeaf based); fruit and vegetable juices and juice flavored beverages as well as juice drinks, nectars, concentrates, punches and "ades"; sweetened and flavored waters, both carbonated and still; sport/energy/health drinks; alcoholic beverages plus alcohol-free and other low-alcohol products including beer and malt beverages, cider, and wines (still, sparkling, fortified wines and wine coolers); other beverages processed with heating (infusions, pasteurization, ultra high temperature, ohmic heating or commercial aseptic sterilization) and hot-filled packaging; and cold-filled products made through filtration or other preservation techniques. The nature and type of the constituents of the foodstuffs or beverages do not warrant a more detailed description here, the skilled person being able to select them on the basis of his general knowledge and according to the nature of said product.

In the case of flavoring compositions, typical concentrations of 5-(2-(1-ethoxyethoxy)propan-2-yl)-2-methyl-2-vinyltetrahydrofuran are in the range of, by weight, of about 0.01% to 15%, particularly from about 1% to about 15%, more particularly from about 1% to about 5%, and more particularly from about 1% to about 2% of the total weight of the compositions. In one embodiment, the concentration of 5-(2-(1-ethoxyethoxy)propan-2-yl)-2-methyl-2-vinyltetrahydrofuran in a flavored article are in the range, by weight, of about 3 ppm to about 60 ppm, particularly from about 3 ppm to about 45 ppm, more particularly from about 3 ppm to about 30 ppm, more particularly from about 12 ppm to about 45 ppm, 12 ppm to about 30 ppm, and even more particularly from about about 12 ppm to about 15 ppm, and even more particularly from about 17 ppm to 33 ppm based on the total weight of the flavored article.

In another embodiment, the compounds provided herein are provided in an amount in a flavored article such that the compounds by weight, acetaldehyde in an amount that ranges from about 1 ppm to about 20 ppm, more particularly from about 1 ppm to about 10 ppm, more particularly from 4 ppm to about 10 ppm, even more particularly from about 4 ppm to about 6 ppm of the total weight of the article.

By "flavor adjuvant" we mean here an ingredient capable of imparting additional added benefit such as a color, a particular light resistance, chemical stability, and so on. A detailed description of the nature and type of adjuvant commonly used in flavoring bases cannot be exhaustive. Nevertheless, such adjuvants are well known to a person skilled in the art, but it has to be mentioned that said ingredients are well known to a person skilled in the art.

For the sake of clarity, it has to be mentioned that, by "foodstuff" we mean here an edible product, e.g. a food or a beverage. Therefore, a flavored article according to the invention comprises one or more compounds according to 5-(2-(1-ethoxyethoxy)propan-2-yl)-2-methyl-2-vinyltetrahydrofuran, as well as optional benefit agents, corresponding to a flavor or aroma profile of the desired edible product, e.g. a savory cube.

Further provided hereto is a spray dried particle comprising 5-(2-(1-ethoxyethoxy)propan-2-yl)-2-methyl-2-vinyltetrahydrofuran.

Further provided herein is a preparation of a spray dried particle comprising: a) preparing a spray dried feed emulsion comprising an emulsifier, maltodextrin, and 5-(2-(1-ethoxyethoxy)propan-2-yl)-2-methyl-2-vinyltetrahydrofuran or one of its pharmacological acceptable salts wherein the emulsion has a buffer that regulates the between 6 and 9. The emulsifiers can be selected from the group consisting off gum Arabic, saponin, and modified starch. The emulsion may also contain optional ingredients. It may in particular further contain an effective amount of a fireproofing or explosion suppression agents. The type and concentration of such agents in spray-drying emulsions is known to the person skilled in the art. One can cite as non-limiting examples of such fireproofing or explosion suppression agents inorganic salts, $C_1$-$C_{12}$ carboxylic acids, salts of $C_1$-$C_{12}$ carboxylic acids and mixtures thereof. Particular explosion suppression agents are, salicylic acid, acetic acid, propionic acid, butyric acid, isobutyric acid, valeric acid, caproic acid, citric acid, succinic acid, hydroxysuccinic acid, maleic acid, fumaric acid, oxylic acid, glyoxylic acid, adipic acid, lactic acid, tartaric acid, ascorbic acid, the potassium, calcium and/or sodium salts of any of the aforementioned acids, and mixtures of any of these. Other optional ingredients include antioxidants, colorants and dyes.

The emulsion can be formed using any known emulsifying method, such as high shear mixing, sonication or homogenization. Such emulsifying methods are well known to the person skilled in the art.

The droplet size d(v, 0.9) of the emulsion is particularly between 1 and 20/μm, more particularly between 1 and 15/μm, and even more particularly between 1 and 10/μm. More particularly, the droplet size remains within the range for at least one day storage at ambient temperature (25° C.).

The viscosity of the emulsion is particularly between 20 and 300 mPas, more particularly between 70 and 200 mPas and even more particularly between 100 and 150 mPas at die temperature at which the atomization step, as defined below, is conducted.

After the emulsion is prepared, it is then spray-dried so as to obtain dry particles. The spray-drying process comprises two steps, the first one being dispersion and the second one being drying. The emulsion is first subjected to an atomization step, during which the emulsion is dispersed in the form of drops into a spraying tower. Any device capable of dispersing the emulsion in the form of drops can be used to carry out such dispersion. For instance, the emulsion can be guided through a spraying nozzle or through a centrifugal wheel disk into the spraying tower. Vibrated orifices may also be used. The size of the capsules is determined by the size of the drops that are dispersed into the tower. If a spraying nozzle is used for dispersing the drops the size may be controlled by the flow rate of an atomizing gas through the nozzle, for example. In the ease where a centrifugal wheel disk is used for dispersal, the main factor for adjusting droplet size is the centrifugal force with which the drops are dispersed from the disk into the tower. The centrifugal force, in turn, depends on the speed of rotation and the diameter of the disk. The feed flow rate of the emulsion, its surface tension and its viscosity are also parameters controlling the final drop size and size distribution. By adjusting these parameters, the skilled person can control the size of the drops of the emulsion to be dispersed in the tower.

One sprayed in the chamber, the droplets are dried using any technique known in the art. These methods are perfectly documented in the patent and non-patent literature in the art of spray-drying. For example, Spray-Drying Handbook, 3rd ed., K. Masters; John Wiley (1979), describes a wide variety of spray-drying methods.

A process provided herein may be performed in any conventional spraying tower. A conventional multi-stage drying apparatus is for example appropriate for conducting the steps of this process. It may comprise a spraying tower, and, at the bottom of the tower, a fluidised bed intercepting partially dried particles alter falling through the tower.

The following Examples are illustrative only and are not meant to be limiting in any manner.

EXAMPLES

Example 1

Synthesis of 5-(2-(1-Ethoxyethoxy)Propan-2-yl)-2-Methyl-2-Vinyltetrahydrofuran

A mixture of linalyl oxide (CAS #1365-19-1) (59 mmol), diethyl ether (50 mL) and p-toluenesulfonic acid (0.06 mmol) was cooled to 5° C. Ethyl vinyl ether (88 mmol) dissolved in diethyl ether (50 mL) was added dropwise over 30 minutes, and the mixture was stirred for 12 hours at room temperature. Five grams of sodium carbonate was added and the mixture filtered. The product was concentrated using a rotary evaporator and purified by Kugelrohr distillation (70-80° C., 40 mTorr) to afford 5.19 g (37% yield) of the product as a colorless oil (equimolar mixture of four diastereomers).

$^1$H NMR (CDCl$_3$, 400 MHz): δ 1.15-1.31 (m, 15H), 1.63-1.76 (m, 1H), 1.79-1.97 (m, 3H), 3.43-3.61 (m, 2H), 3.82-3.94 (m, 1H), 4.94-5.07 (m, 2H), 5.14-5.22 (m, 1H), 5.81-6.00 (overlapping dd, 1H).

MS (EI): 242 (M$^+$, 0), 169 (2), 153 (38), 111 (46), 93 (27), 85 (18), 81 (24), 73 (100), 71 (31), 45 (39), 43 (47).

Example 2

Synthesis of Comparative Sample 1: 1-Ethoxyethtyl Acetate

Diethyl ether (50 mL), glacial acetic acid (10 g, 167 mmol) and pTSA (0.01 g) were combined and the mixture was cooled in an ice bath. Ethyl vinyl ether (18 g, 250 mmol) in 50 mL of diethyl ether was added dropwise over 15 minutes. The mixture was removed from the cold baths and stirred for two hours at room temperature. Sodium carbonate (5 g) was added and the mixture was filtered. Diethyl ether was removed by fractional distillation at atmospheric pressure. Fractional distillation of the residue yielded 17.7 g (34-35° C., 19 mbar) of 1-ethoxyethyl acetate (134 mmol, 80% yield).

$^1$H NMR (CDCl$_3$, 400 MHz): δ 1.21 (t, J=7.1 Hz, 3H), 1.40 (d, J=5.2 Hz, 3H), 2.07 (s, 3H, 3.49-3.77 (m, 2H), 5.93 (q, J=5.2 Hz, 1H).

MS (EI): 132 (M$^+$, 0), 131 (<1), 117 (3), 89 (5), 87 (12), 73 (55), 45 (61), 43 (100).

Example 3

Assessment of Hydrolysis Rate at pH 3.0

Instant beverage applications require rapid hydrolysis of the precursor molecules in order to rapidly release acetaldehyde. Because such beverages might be consumed immediately upon preparation, it is desired for the release to be as rapid as possible.

A pH 3.0 buffer solution was prepared by adding 16.43 g citric acid (CAS 77-92-9) and 4.26 g disodium citrate (CAS 144-33-2) to 1 L of deionized water. Aliquots of the Example 1-2 preparations were added to the buffer solution within a Distek 2100B USP 2 dissolution system stirring at 200 rpm. The concentration of acetaldehyde in solution was monitored as a function of time using a UV/V is spectrometer probe which measured absorbance at 276 nm every 1 second. Release followed a first order kinetics and half lives are reported in Table 1. Results for comparative samples were taken from work by Gassenmeier et al. [1]. A sample of acetaldehyde diethyl acetal was also measured directly and the result was similar to that reported by Gassenmeier et al. Example 1 released acetaldehyde faster than Comparative Samples 2-5.

TABLE 1

Half life of acetaldehyde precursors at pH 3

| Compound | Half life(s) at pH 3.0 |
|---|---|
| Example 1: 5-(2-(1-ethoxyethoxy)propan-2-yl)-2-methyl-2-vinyltetrahydrofuran | 164 |
| Comparative Sample 1: 1-ethoxyethyl acetate | 31 |
| Comparative Sample 2: Acetaldehyde diethyl acetal (measured for this work) | 539 |
| Comparative Sample 3: Acetaldehyde diethyl acetal [1] | 579 |
| Comparative Sample 4: 1-ethoxy-1-(1-ethoxy-ethoxy)-ethane [1] | 306 |
| Comparative Sample 5: 4,6,9-trimethyl-3,5,8,10-tetraoxadodecane (Aldemax ®) [1] | 625 |

[1] Gassenmeier, K., Daniher, A., Furrer, S., 1-Ethoxy-1-(1-ethoxy-ethoxy)-ethane: a new acetaldehyde precursor, in: Wender, L.P.B. (Ed.), Developments in Food Science Flavour Science Recent Advances and Trends, Elsevier, 2006, pp. 305-308.

Example 4

Assessment of Hydrolysis Rate Under Spray Drying Feed Conditions

Acetaldehyde precursors suitable for rendering into dry powders must avoid releasing significant levels of acetaldehyde during various stages of processing. In particular they should resist hydrolysis during the preparation of a spray drying feed emulsion, which can be neutral to basic pH and can contain a significant volume fraction of an oil phase.

A pH 8.0 buffer solution was prepared by adding 49.92 g disodium phosphate heptahydrate (CAS 7782-85-6) and 1.93 g monosodium phosphate (CAS 7558-80-7) to 1 L of deionised water. Aliquots of 0.20 g the Example 1-2 preparations were dissolved in 0.8 g of limonene (CAS 5989-25-7) added to 10 g of the buffer solution within a 30 mL Erlenmeyer flask containing a stir bar. The concentration of acetaldehyde in solution was monitored as a function of time using a UV/Vis spectrometer probe measuring absorbance at 276 nm. Stirring was periodically stopped to allow oil droplets to rise to the surface and collect an unobscured absorbance reading of the aqueous solution. Release followed mixed zero and first order kinetics. $t_{50}$ (the time to 50% of the maximum absorbance) values are reported in Table 2. Example 1 experienced no measurable increase in absorbance over 1 hour, which indicates that release of acetaldehyde did not occur. Comparative Sample 1 has $t_{50}$ of 2.1 minutes, which is so short that a person skilled in the art would consider this compound at risk of experiencing a problematic degree of hydrolysis during processing. Example 1 has a much longer $t_{50}$ value and released acetaldehyde more slowly than Comparative Sample 1.

TABLE 2

$t_{50}$ of acetaldehyde precursors at pH 8 in emulsions

| Compound | $t_{50}$ at pH 8.0 |
|---|---|
| Example 1: 5-(2-(1-ethoxyethoxy)propan-2-yl)-2-methyl-2-vinyltetrahydrofuran | >>1 hour |
| Comparative Sample 1: 1-ethoxyethyl acetate | 2.1 min |

Example 5

Preparation of Spray Dried Powder

Spray drying feed emulsions were prepared according to Table 3. The amount of the precursor molecule was chosen to produce 0.25 g acetaldehyde based on stoichiometry. The Example 1 liquid was dissolved into the orange flavor. This mixture was added to the salt, maltodextrin, water and saponin solution and mixed for 2 minutes using a homogenizer (T25 UltraTurrax, IKA Works, USA). The preparation was then spray dried (model 190 Mini-Spray Drier, Buchi Corporation, New Castle Del., USA) with inlet air temperature set to 138° C. and outlet air temperature of 95° C.

TABLE 3

Spray drying feed formula

| Compound | Spray Dry A | Spray Dry B |
|---|---|---|
| Example 1: linalyl oxide acetal | 1.41 g | — |
| Nat Orange WONF (596407 A) 567407A, Firmenich Inc, Plainsboro, NJ, USA) | 8.40 g | 8.40 g |
| Maltodextrin (Glucidex IT 19, Roquette Corporation, Lestrem, France) | 40.5 g | 40.5 g |
| Deionised water | 40.5 g | 40.5 g |
| Monosodium phosphate (CAS 7558-80-7) | 0.05 g | 0.05 g |
| Disodium phosphate heptahydrate (CAS 7782-85-6) | 0.50 g | 0.50 g |
| Saponin solution (Q-Naturale 200, Ingedion Incorporated, West Chester, IL, USA) | 1.00 g | 1.00 g |

Example 6

Preparation and Evaluation of Instant Beverages

Spray Dry preparations A & B were reconstituted by combining 0.1 g of the preparation with 0.07 g citric acid, 7 g sucrose and dissolving the mixture in 100 mL of distilled water. The beverages were prepared quickly and tasted by a panel of 5 individuals. The spray dried A sample was found to be fresher and riper than the beverage prepared from Spray Dry B.
1) Analysis of Acetaldehyde Yield The concentration of acetaldehyde derived from Spray Dry A & B was measured using reverse phase HPLC after dissolving the powder in water and derivatizing with 2,4-dinitrophenylhydrazine. Results in Table 4 show that high levels of acetaldehyde are liberated from Spray Dry powder A.

TABLE 4

Acetaldehyde concentration in spray dried powders

| Powder | Acetaldehyde concentration fresh (g/100 g) |
|---|---|
| Spray Dry A: 5-(2-(1-ethoxyethoxy)propan-2-yl)-2-methyl-2-vinyltetrahydrofuran | 0.51 |
| Spray Dry B: control - orange oil | 0.05 |

What is claimed is:

1. A compound of the formula: 5-(2-(1-ethoxyethoxy)propan-2-yl)-2-methyl-2-vinyltetrahydrofuran.

2. A method of releasing acetaldehyde into an aqueous solution comprising delivering 5-(2-(1-ethoxyethoxy)propan-2-yl)-2-methyl-2-vinyltetrahydrofuran to the aqueous solution.

3. A flavor-modifying composition comprising:
   i) the 5-(2-(1-ethoxyethoxy)propan-2-yl)-2-methyl-2-vinyltetrahydrofuran of claim 1;
   ii) at least one ingredient selected from the group consisting of a flavor carrier and a flavor base; and
   iii) optionally at least one flavor adjuvant.

4. A flavored article comprising:
   i) the 5-(2-(1-ethoxyethoxy)propan-2-yl)-2-methyl-2-vinyltetrahydrofuran of claim 1; and
   ii) a foodstuff base.

5. The flavored article of claim 4, wherein the flavored article is a food or beverage product.

* * * * *